United States Patent [19]

Jones et al.

[11] Patent Number: 4,933,168

[45] Date of Patent: Jun. 12, 1990

[54] STABLE, CRYSTALLINE FLUNISOLIDE

[75] Inventors: Richard E. Jones, Palo Alto; Gisela T. Haringer, Watsonville, both of Calif.

[73] Assignee: Syntex Pharmaceuticals International Limited, Hamilton, Bermuda

[21] Appl. No.: 301,922

[22] Filed: Sep. 14, 1981

Related U.S. Application Data

[60] Continuation-in-part of Ser. No. 40,831, May 21, 1979, abandoned, which is a continuation-in-part of Ser. No. 931,070, Aug. 4, 1978, abandoned, which is a continuation of Ser. No. 743,250, Nov. 19, 1976, abandoned, which is a continuation of Ser. No. 736,630, Oct. 28, 1976, abandoned, which is a division of Ser. No. 581,300, Aug. 27, 1975, abandoned.

[51] Int. Cl.$^5$ .................. A61K 31/58; C07J 71/00; A61L 9/04

[52] U.S. Cl. ........................ 424/45; 540/63; 514/174

[58] Field of Search ................. 424/243, 45; 260/397.45; 540/63; 514/174

[56] References Cited

U.S. PATENT DOCUMENTS

| | | | |
|---|---|---|---|
| 3,126,375 | 3/1964 | Ringold et al. | 260/239.55 |
| 3,197,469 | 7/1965 | Fried | 260/239.55 |
| 3,282,791 | 11/1966 | Macek | 424/214 X |
| 4,044,126 | 8/1977 | Cook et al. | 424/243 |
| 4,293,710 | 6/1981 | Jones et al. | 260/239.55 D |
| 4,364,923 | 12/1982 | Cook et al. | 424/45 |

*Primary Examiner*—Joseph A. Lipovsky
*Attorney, Agent, or Firm*—Elizabeth Manning; Tom Moran; Alan Krubiner

[57] ABSTRACT

A unique crystalline polymorphic form of flunisolide is disclosed which is stable in aerosols such as Freon ® mixtures and is valuable in the treatment of respiratory diseases, particularly bronchial asthma and allergic rhinitis.

11 Claims, No Drawings

STABLE, CRYSTALLINE FLUNISOLIDE

This application is a continuation-in-part of application Ser. No. 40,831, filed May 21,1979, now abandoned, which, in turn, is a continuation-in-part of application, Ser. No. 931,070, filed Aug. 4, 1978, now abandoned, which in turn is a continuation of U.S. Ser. No. 743,250, filed Nov. 19, 1976, now abandoned, which in turn is a continuation of U.S. Ser. No. 736,630, filed Oct. 28, 1976, now abandoned, which in turn is a division of U.S. Ser. No. 581,300, filed May 27, 1975, now abandoned.

BACKGROUND OF THE INVENTION

1. Field of the Invention

This invention relates to flunisolide hemihydrate, treatment of inflammatory or infectious diseases of the respiratory tract using it and therapeutically useful preparations containing it.

2. Prior Art

Flunisolide is the common name of a known compound, 6α-fluoro-11β,21-dihydroxy-16α,17α-isopropylidenedioxypregna-1,4-diene-3,20-dione. Its structural formula is, thus,

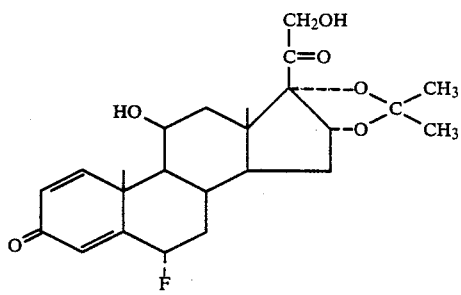

Procedures for making compounds of this type are described in U.S. Pat. No. 3,126,375 to Ringold et al. Flunisolide has anti-inflammatory and anti-pyretic activity and has had primary utility in the treatment of topical inflamed conditions. The compound is previously unknown to be polymorphic but it has now been discovered that there are several polymorphic forms. In addition, the hemihydrate of the formula

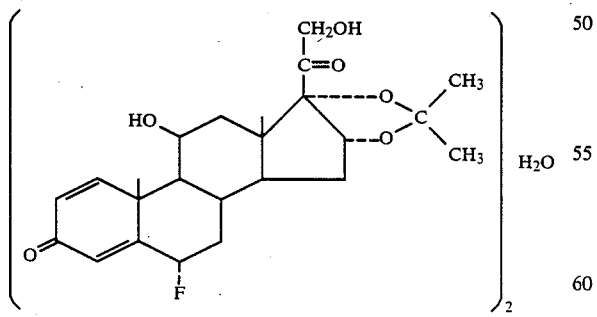

is particularly stable in the presence of aerosol propellants so that it may be readily formulated to form an aerosol which is particularly valuable in the treatment of respiratory diseases such as bronchial asthma, allergic rhinitis, and others which respond to treatment by suitable steroids.

It is generally known in the art that certain specific steroids may be used for the treatment of asthma, for example, hydrocortisone and prednisolone have been used as an aerosol suspension. (See for example *J. Allergy*, 29 (3), 214–221, 1958.) Other steroids which have been used in various formulations include dexamethasone phosphate (See U.S. Pat. No. 3,282,791 to Macek; *J. Allergy*, 34 (2), 119–126, March-April, 1963), betamethasone 17-valerate (see *JAMA*, 231 (4), 406–407, Jan. 27, 1975) and triamcinolone acetonide (see *J. Allergy*, 33 (1), 1–5, January-February, 1962 and *American Review of Respiratory Disease*, 109, 538–543, 1974). It is also known that beclomethasone dipropionate (9α-chloro-16α-methyl-prednisolone-17α,21-dipropionate) along with certain other steroids such as fluocinolone acetonide (6α,9α-difluoro-11β,21-dihydroxy-16α,17α-isopropylidenedioxy-pregna-1,4-diene-3,20-dione) may be used in aerosol formulations as taught in German Offenlegungschrift No. 2,320,111. However, that patent teaches that if these steroids are placed in the aerosol formulation without previous treatment the particles tend to increase in size and deposit on the sides of the can or along the throat of the release tube and may ultimately plug the tube or change the concentration of the aerosol released. Thus, that patent teaches that if the steroid is first solvated according to the process described, the solvated steroid does not tend to increase in particle size nor drop out of the dispersion in the aerosol formulation.

Surprisingly, it has now been found that a flunisolide hemihydrate is stable in aerosol formulations which use suitable fluorinated and chlorinated hydrocarbon propellants. This heretofore unknown compound, because of these properties, is useful in the treatment of bronchial asthma, allergic rhinitis or other respiratory ailments.

DESCRIPTION OF THE INVENTION

The flunisolide hemihydrate exhibits a powder X-ray diffraction pattern shown in Table A below.

TABLE A

| d Å | I/I₁ % | θ deg. |
|---|---|---|
| 10.04 | 50 | 4.4 |
| 9.82 | 60 | 4.5 |
| 9.30 | 80 | 4.8 |
| 7.69 | 50 | 5.8 |
| 6.91 | 50 | 6.4 |
| 6.32 | 10 | 7.0 |
| 5.98 | 90 | 7.4 |
| 5.53 | 100 | 8.0 |
| 5.21 | 60 | 8.5 |
| 5.06 | 60 | 8.8 |
| 4.79 | 10 | 9.3 |
| 4.55 | 70 | 9.8 |
| 4.33 | 1 | 10.3 |
| 4.13 | 10 | 10.8 |
| 3.95 | 10 | 11.3 |
| 3.86 | 5b | 11.5 |
| 3.70 | 5 | 12.0 |
| 3.63 | 10 | 12.3 |
| 3.36 | 1 | 13.3 |
| 3.30 | 2 | 13.5 |
| 3.21 | 2 | 13.9 |
| 3.03 | 1 | 14.8 |
| 2.88 | 2 | 15.5 |
| 2.67 | 2b | 16.8 |
| 2.63 | 1 | 17.0 |
| 2.60 | 1 | 17.3 |
| 2.56 | 1 | 17.5 |
| 2.40 | 3 | 18.8 |
| 2.31 | 1 | 19.5 |
| 2.28 | 1 | 19.8 |

TABLE A-continued

| d Å | I/I$_1$ % | θ deg. |
|---|---|---|
| 2.13 | 1 | 21.3 |
| 2.10 | 1 | 21.5 |
| 1.97 | 1 | 23.0 |
| 1.88 | 2 | 24.3 |

A general discussion of the theory and definitions as well as the general procedure of X-ray diffractometry is set forth in the monograph at pages 902-904 of the *National Forumlary XIII*.

The above X-ray diffraction pattern was made using a Siefert Debeyflex Universal X-ray generator Catalog No. 2200 having a copper anode tube with a nickel filter and a 35 mm Nonius camera having a 114.6 mm diameter. The readings were taken using the ground powder of flunisolide placed in a suitable capillary tube having an inside diameter of about 0.5 mm mounted in the X-ray beam. The crystal structure of the ground flunisolide exhibits a regular 3-dimensional pattern which is defined numerically in Table A. In Table A the symbol "d" is the interplanar spacing, that is the distance between parallel planes in which the atoms of the crystal lie. The spacing between the planes in the 3-dimensional lattice is determined from the X-ray diffraction. The dimensions of the spacings are given in terms of angstroms (Å). "θ" is one half the angle between the primary beam projection and the diffracted beam while the ratio "I/I$_1$" is the relative intensity of an X-ray maxima in which "I" is the intensity of the maximum corresponding to the indicated "d" value, and "I$_1$" is the intensity of the strongest maximum of the pattern. The intensities in this case, in which a film was used, were compared with a calibrated scale.

As pointed out in the above monograph in the *National Formulary XIII*, in powder diffraction work, intensity data are intended only as a guide to strong and weak X-ray maximum. They may vary much from laboratory to laboratory by as much as about 25%. Further, the errors in data for interplanar spacings ("d") value) vary according to the size of the spacing. The error in "d" is inversely proportional to "θ". Variation of the observed "d" value from those given in the Table A are permissible up to a magnitude equivalent to ±0.3° θ (for a copper target X-ray tube), which was used in the determination of flunisolide hemihydrate.

Flunisolide hemihydrate is of course further characterized by the presence of 2.0 ±0.2% by weight water, as determined by Karl Fischer analysis. (The calculated stoichiometric value of the percentage of water by weight for a hemihydrate of flunisolide is 2.03%.) The percent water determined in this way remains constant, regardless of the water content of the crystallizing solvent.

Analysis of the hemihydrate for water content is done by any suitable analytical method. Generally analysis is done using Karl Fischer reagent. The Karl Fischer analysis for water may be performed according to the original method set forth in Angewandte Chemie, 48, 394 (1935). Preferably, however, the analysis is performed using Photovolt Corporation's automatic analyzer, Aquatest IV. The Aquatest IV is a coulometric titrator which incorporates microprocessor control and is based on the specific and quantitative reaction of water with Karl Fischer reagent. The instrument is unique in that the reagent is generated electronically which eliminates the need for standardization or calibration. The accuracy of the instrument is within ±10 micrograms (mcg) or 1% which ever is greater. For determination of water in flunisolide hemihydrate, where the sample sizes chosen for the determinations are between 35 mg and 75 mg and contain between 700 mcg and 1500 mcg of water, the accuracy is within ±0.03% of the amount of water determined in mcg. The microprocessor control serves to distinguish between the titration of water which is in the sample and any effect which is oxidizing or reducing in character. The Aquatest IV is operated as described in the instruction manual published by Photovolt Corporation in July 1978 and by Paper No. 260 presented at the Pittsburg Conference on Analytical Chemistry and Applied Spectroscopy in February of 1978 by K. A. Lindblom. The address of Photovolt Corporation is 1115 Broadway, New York, N.Y. 10010.

Preparation of Flunisolide Hemihydrate

It was not heretofore known that flunisolide existed in polymorphic forms, thus each of the forms defined hereinafter are newly recognized entities.

A compound loses its crystalline identity when going into solution. It has been found that the hemihydrate is formed when flunisolide is recrystallized from a solution of halogenated hydrocarbon such as methylene chloride when there is sufficient moisture present to be incorporated into the crystalline structure.

The process simply entails dissolving any of polymorphic forms of flunisolide in the solvent and forcing the crystals of the flunisolide hemihydrate to develop. The crystallization may be done by forcing the compound out of solution, e.g. by cooling or by adding solvent in which flunisolide is less soluble, such as a suitable aliphatic or aromatic liquid hydrocarbons. Representative aromatic hydrocarbons include benzene, toluene, and the like, while suitable aliphatic hydrocarbons include those of medium carbon chain length, e.g. 6–12 carbons and may be branched or straight hydrocarbon. Examples are iso-octane, hexane, heptane, nonane, decane or octane and the like. Iso-octane, i.e. 2,2,4-trimethyl pentane, is particularly effective. Although there is generally enough moisture present in the air and solvent to form the hemihydrate, sufficient water is preferably added to the solvents to assure the formation of the hemihydrate. This amount is generally about 0.05 to 5% by volume of the solvents used and preferably is about 0.1 to 1% by volume.

Flunisolide hemihydrate is also prepared by contacting another micronized polymorphic form of flunisolide with a suitable non-solvent liquid in the presence of water. In this process, it appears that the hemihydrate is formed by an internal crystalline rearrangement without an intermediate destruction of the old crystalline structure and without further particle growth. Compounds found to be particularly valuable for effecting the conversion are the halogenated lower aliphatic hydrocarbons, especially those known as Freon ® propellants, a trademark for a group of halogenated hydrocarbons (usually based on methane or ethane) containing one or more fluorine atoms widely used as non-toxic propellants. Particularly useful are, Freon 12 (dichlorodifluormethane), Freon 114 (dichlorotetrafluoroethane) and mixtures of these two as well as mixtures of these two with other freons such as Freon 11 (trichloromonofluoromethane), Freon 22 (monochlorodifluoromethane), Freon 113 (trichlorotrifluoroethane), Freon 21 (dichloromonofluoroethane), Freon 13 (monochlorotrifluoromethane), Freon C318 (octafluorocyclobutane), Freon 115 (monochloropentafluoroethane), and the like. Other compounds which may be included are non-toxic, lower alkanes containing up to 5 carbons such as butane or pentanes.

Flunisolide hemihydrate may be prepared either prior to forming the aerosol formulation or it may be prepared by contacting a micronized form in a suitable-sized particle with the propellant under conditions suitable for maintaining the propellant as a liquid. Since the hemihydrate of flunisolide is formed by contact with certain liquid propellants (e.g. Freon 11) which are ultimately used for the formulation, it may not be necessary to first prepare the hemihydrate before formulating. All that is required is to mill flunisolide to the desired particle size, i.e. less than about 100 microns, more suitably less than about 25 microns and preferably less than about 5 microns.

It appears that the conversion of the other polymorphic forms of flunisolide to the hemihydrate begins soon after contact with the suitable liquid compound. Substantially complete conversion is obtained in two weeks or less at room temperature and about 50 psig in the Freons and normal humidity. In Freon 11 with Span ® 85 surfactant conversion occurs in less than a half hour at room temperature and atmospheric pressure. Since the Freon propellants are generally gaseous at room temperature care must be taken to employ conditions which will retain the Freons as a liquid. Thus temperatures below their boiling point must be employed or the compounds must be kept under pressure sufficient to maintain the compounds as liquids. This is generally done simply by employing methods known in the art for preparing aerosols. The flunisolide is first micronized to the desired particle size and the aerosol "bombs" or dispensers are prepared according to known methods as discussed hereafter. Thus, if the flunisolide is not the hemihydrate to begin with, the conversion takes place after the aerosol dispenser is prepared.

The preferred method of preparing flunisolide hemihydrate comprises crystallizing flunisolide from a solution of an aqueous alkanol of three or more carbon atoms. Because alkanols of greater than four carbon atoms are less volatile than alkanols of four or less carbon atoms and therefore are more difficult to remove, alkanols of 3 or 4 carbons are preferred. Alkanols of 3 or 4 carbon atoms include, for example, isopropanol, n-propanol, n-butanol, isobutanol, and the like. The alkanols is aqueous, that is, it contains about one to ten percent water by volume, and preferably contains two to five percent water by volume.

The flunisolide solution can be obtained in several ways. Any polymorphic form of flunisolide can be added to the alkanol or the alkanol can be added to the crystalline form and agitated until the flunisolide is entirely in solution. Thereafter, the desired amount of water can be added. In order to speed the process of solution the alkanol can be heated to a temperature of up to its boiling point (e.g. n-butanol is about 117° C.). Alternatively, the alkanol can be added to an existing solution of flunisolide in another solvent with a lower boiling point than the alkanol. For example, n-butanol can be added to a solution of flunisolide in methylene chloride and the methylene chloride distilled off while n-butanol becomes the solvent for flunisolide. This is done through the simple expedient of replacement distillation. It is important of course, to use sufficient alkanol to keep the flunisolide in solution. Water is added as needed to give about 2-5% v/v water. Thus, the concentration of flunisolide will vary with the alkanol used. It has been found that about 50 grams of flunisolide will dissolve at 80° C. in 250 milliliters (ml) of n-butanol containing 2% v/v water and crystallize from solution at about 35° C.

Once a solution of flunisolide in the alkanol is obtained, the crystallization of the flunisolide hemihydrate is effected, preferably at a temperature of less than about 75° C. For example, this can be done by allowing an aqueous n-butanol solution to slowly cool, e.g., at a rate of 1° every 30 seconds to about 10 minutes. The initial temperature of the aqueous alkanol solution can be anywhere from about 30° C. to about the boiling point of the alkanol.

Although the desired flunisolide hemihydrate is obtained by allowing the crystallization through cooling alone, such a process may not always be economically advantageous because of the large amount of flunisolide remaining in solution. Thus, a suitable alkane solvent (in which flunisolide has little solubility) may be added to the alkanol solution to force the flunisolide hemihydrate from solution. The alkane solvent is preferably n-hexane or n-heptane. Generally the volume of n-hexane or n-heptane which is added is about twice to about five times the volume of the alkanol solution, and is added slowly to the alkanol solution over an extended period of time, e.g. about 10 minutes to 4 hours or more, depending on the volumes of the solvents involved. For example, 750 ml of n-hexane may be added to about 250 ml of an aqueous n-butanol flunisolide solution over an hour. The alkane solvent may be the same temperature as the n-butanol solution, or less, but preferably is at ambient temperature, i.e., about 20°–25° C. to speed the crystallization.

Once the flunisolide hemihydrate crystals are obtained, they are dried by means known in the art such as vacuum drying to remove any solvent. This may be done for a period of 2 hours to several days.

As pointed out previously, it has been found that flunisolide hemihydrate is formed by contacting any of the other polymorphic forms of flunisolide with the suitable solvent as delineated above. It is surprising to find that this occurs since upon heating flunisolide hemihydrate to about 200° and cooling the crystals back to room temperature, the hemihydrate is destroyed and flunisolide form B results. This seems to be the most stable form as a free solid, that is under air. Form B has the X-ray diffraction pattern as set forth in Table B.

TABLE B

| d Å | I/I$_1$ % | θ deg. |
|---|---|---|
| 8.84 | 1 | 5.0 |
| 7.82 | 80 | 5.6 |
| 7.08 | 60 | 6.3 |
| 6.80 | 60 | 6.5 |
| 6.32 | 70 | 7.0 |
| 6.10 | 80 | 7.3 |
| 5.90 | 80 | 7.5 |
| 4.79 | 100 | 9.3 |
| 4.44 | 100 | 10.0 |
| 4.13 | 1 | 10.8 |
| 3.78 | 1 | 11.8 |
| 3.49 | 1 | 12.8 |
| 3.08 | 5 | 14.5 |
| 2.88 | 1 | 15.5 |
| 1.78 | 50 | 26.0 |
| 1.73 | 2 | 26.5 |

TABLE B-continued

| d Å | I/I₁ % | Θ deg. |
|---|---|---|
| 1.70 | 2 | 27.0 |

Another polymorphic form referred to herein as Form C also exists which may be substantially pure flunisolide or it may exist with a certain amount of methanol included in the holes of this particular crystal lattice, thus forming a methanol clathrate. The X-ray diffraction pattern of Form C is given in Table C. Form C may also be converted into stable form B upon heating to 200° C. and cooling to room temperature.

TABLE C

| d Å | I/I₁ % | Θ deg. |
|---|---|---|
| 13.59 | 10 | 3.3 |
| 8.84 | 1 | 5.0 |
| 7.37 | 20 | 6.0 |
| 6.65 | 100 | 6.6 |
| 6.10 | 2 | 7.3 |
| 5.43 | 80 | 8.2 |
| 4.92 | 5 | 9.0 |
| 4.67 | 5 | 9.5 |
| 4.13 | 10 | 10.8 |
| 3.78 | 1 | 11.8 |
| 3.52 | 5 | 12.6 |
| 3.19 | 1 | 14.0 |
| 3.13 | 1 | 14.3 |
| 2.88 | 1 | 15.5 |
| 2.79 | 1 | 16.0 |

Treatment of Respiratory Diseases Using Flunisolide Hemihydrate

Flunisolide hemihydrate is useful in the treatment of inflammatory or infectious diseases of the respiratory tract (respiratory diseases) such as bronchial asthma, bronchitis, pneumonitis, occupational respiratory diseases, allergic rhinitis, nasal polyps, hay fever, and the like.

The process of treating a person with a respiratory disease comprises administering by inhalation a therapeutically effective amount of flunisolide hemihydrate to a person having a respiratory disease which responds to treatment by the organic portion of flunisolide hemihydrate. The inhalation may be either bronchially via the oropharynx (orally) or nasally but is such that a sufficient amount of the compound is administered to the afflicted area to cause an improvement in the condition. The portion of the respiratory tract afflicted may be the nasal chambers, trachea, bronchi, lower air passages, or bronchioles.

In treating respiratory tract allergies which are located generally primarily in the nasal area such as allergic rhinitis, nasal polyps or seasonal hay fever, a therapeutically effective amount of Flunisolide is sprayed into the nasal chamber, usually while the person is inhaling through the nose, although inhalation is not necessary in each case.

A therapeutically effective amount for such nasal afflictions is about 0.01 milligrams (mg) to about 5 mg per person per day, preferably about 0.05 to about 0.25.

In the case of affliction of the trachea, bronchi, or bronchioles the active ingredient is most effectively administered by releasing a metered dosage of mist within the mouth of the patient and having the patient inhale at substantially the same time so that the aerosol is taken into the mouth and through the respiratory tract, to the lungs thereby administering the active ingredient to the respiratory tract. A therapeutically effective dosage will be about 0.5 milligrams (mg) to about 5 mg per person per day and preferably will be about 0.5 to 2 mg per person per day.

Whether given orally or nasally, the amount may be administered all at one time or in several smaller portions at designated times during the day. The small portions may be anywhere from 0.01 to 1.0 mg. per application. The exact dosage will vary with, i.a., the severity of the condition, the particular formulation used, other drugs used, and the individual involved.

Aerosol Formulations with Flunisolide Hemihydrate

Aerosol formulations which may be effective are set forth in U.S. Pat. No. 3,014,844 to Thiel and in U.S. Pat. No. 3,282,791 to Macek, the flunisolide hemihydrate being substituted for the active ingredients disclosed therein. Thus, suitable formulations include a sufficient amount of the flunisolide hemihydrate in combination with an effective amount of an aerosol propellant and an acceptable surface active agent. If propellants are employed which do not convert the other polymorphic forms of flunisolide to the hemihydrate after formulation, the hemihydrate is first prepared and then is formulated. Preferably Freon 11 will be used in the formulation, obviating the need for prepreparation of flunisolide hemihydrate prior to formulation.

Contrary to the teaching of the German patent which requires the solvation of beclomethasone dipropionate or fluocinolone acetonide before formulation, flunisolide need not be solvated prior to formulation since, surprisingly, flunisolide hemihydrate does not appear to be plagued with problems of crystal growth in the aerosol formulated.

Generally, flunisolide hemihydrate will be a finely-divided solid material or powder suspended in a suitable liquified propellant, which also serves as a suspending medium, with a nonionic surface active agent which is a liquid at ambient temperatures.

More specifically, for aerosol administration in the process of this invention the active ingredient is generally a finely-divided powder and may constitute from about 0.01 to about 20% by weight of the total composition. A particularly suitable range is about 0.02 to about 10% and preferably the range will be about 0.04 to about 1.0% by weight of the total composition.

Preferably, the particle size of the finely-divided solid powder is less than 100 microns and more suitably should be less than 25 microns, preferably less than 5 microns in diameter. The particles should be large enough so that they are deposited in the respiratory tract and not entirely exhaled by the patient after inhalation. Also for best results, the size of the particles of powder should be substantially uniform.

Also present is a surface active agent which may constitute from about 0.1 to about 20% by weight, desirably between 0.25 and 5%, and preferably for purposes of treating respiratory diseases between about 0.25 and 1.5% by weight of the total composition, the remainder of the composition being the liquified propellant.

The surfactant employed is preferably a liquid, nonionic, surface-active agent and should have a hydrophile lipophile balance (HLB) ratio of less than 10. The HLB ratio is an empirical number which provides a guide to the surface-active properties of a surface-active agent. The lower the HLB ratio, the more lipophilic is the agent, and conversely, the higher the HLB ratio, the more hydrophilic is the agent. The HLB ratio is well known and understood by the colloid chemist and its method of determination is described by W. C. Griffin in the Journal of the Society of Cosmetic Chemists, Vol. 1, No. 5, pages 311-326 (1949). Preferably the surface-active agent employed should have an HLB ratio of about 1 to 5. It is possible to employ surface-active agents which themselves do not possess an HLB ratio within these ranges, providing they are used in conjunction with other surface-active agents which have an HLB ratio which will provide a mixture having an HLB ratio within the prescribed range.

Those surface-active agents which are soluble or dispersible in the propellant are effective. The more propellant-soluble surface-active agents are the most effective. It is also important that the surface-active agent should be non-irritating and non-toxic.

We have found that among the liquid non-ionic surface-active agents which may be employed in our compositions are the esters or partial esters of fatty acids containing from 6 to 22 carbon atoms, such as caproic, octanoic, lauric, palmitic, stearic, linoleic, linolenic, oleostearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate).

Specific examples of other surface-active agents which may be employed are
Sorbitan monolaurate,
Polyoxyethylene sorbitol tetraoleate,
Polyoxyethylene sorbitol pentaoleate.

The liquified propellant employed may be one which is a gas at room temperature (65° F.) and atmospheric pressure (760 mm of mercury), i.e., it may have a boiling point below 65° F. at atmospheric pressure and is non-toxic. Among the suitable liquified propellants which may be employed are the lower alkanes containing up to five carbons, such as butane and pentane. The most suitable liquified propellants are the fluorinated and fluorochlorinated lower alkanes such as are sold under the trademark "Freon". Mixtures of the above mentioned propellants may suitably be employed.

It is contemplated that the fluorinated or fluorochlorinated lower alkane shall contain not more than 4 carbon atoms and at least one fluorine atom. The preferred halogenated lower alkane compounds may be represented generally by the formula $C_mH_nCl_yF_z$, wherein m is an integer less than 5, n is an integer or zero, y is an integer or zero, and z is integer, such that $n+y+z=2m+2$. Examples of these propellants are dichlorodifluoro methane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), monochloropentafluoroethane ("Freon 115"), octofluorocyclobutane ("Freon C318"), and monochlorotrifluoromethane ("Freon 13"). Propellants with improved vapor pressure characteristics may be obtained by using certain mixtures of these compounds, e.g. "Freon 11" with "Freon 12" or "Freon 12" with "Freon 114". For example, dichlorodifluoromethane, which has a vapor pressure of about 70 pounds per square inch gauge and 1,2-dichloro-1,1,2,2-tetrafluoroethane ("Freon 114"), with a vapor pressure of about 13 pounds per square inch gauge at 70° F., may be mixed in various proportions to form a propellant having an intermediate vapor pressure which is well suited for use in relatively low pressure containers.

It is most desirable that the vapor pressure of the propellant (or mixture of propellants) employed shall itself be between about 25 and 65 pounds per square inch gauge at 70° F., and preferably between about 35 and 55 pounds per square inch gauge at that temperature. A one-component propellant defined for use in the composition may give a composition with gauge pressures in the range of 55 to 65 pounds per square inch at 70° F., which are usable safely with metal container. The two-component propellants, such as equal weight mixtures of "Freon 12" and "Freon 11", may give gauge pressures in the range of 20 to 40 pounds per square inch at 70° F., which are usable safely with specially reinforced glass containers.

It is usually desirable to keep the gas pressure as low as possible, within the limits imposed by the desired specific gravity of the propellant, in order to enable simple containers to be used safely and to prevent too high a pressure causing too wide a dispersal of the powder aerosol. When stronger containers, for example of stainless steel or aluminum, can be used and the active solid medicament is intended for pulmonary inhalation, it is advantageous to use a propellant with a gauge pressure of between 40 and 50 pounds per square inch; this allows complete aerosolization before the stream reaches the back of the throat. Since the powder is already present in the composition dispersed in the desired particle size, there is no need for further breakup action in the valve or applicator, so valves of simple construction may be used, and there is no need to provide special nozzles and expansion chambers, as is usually required when dispensing materials which are dissolved in the propellant, or in a liquid which is emulsified with the propellant.

In producing useful aerosols, a container equipped with a suitable valve is first filled with a suitable propellant containing the finely-divided powder in suspension. A container may first be charged with a weighed amount of dry powder which has been ground to a predetermined particle size or in a slurry of powder in the cooled liquid propellant. Alternately and preferably, the powder in the surface active agent may be triturated or homogenized first into a uniform paste, for instance, by pestle and mortar. This paste is then dispersed in the cooled liquified propellant. This procedure fosters uniform wetting of the powder particles. A container may also be filled by introducing powder and propellant by the normal filling method of a slurry of the powder in that component of the propellant which boils above room temperature may be placed in the container, the valve sealed in place, and the balance of the propellant may be introduced by pressure filling through the valve nozzle.

On operating the valve of the finished dispenser the powder will be dispensed in a stream of propellant which will vaporize providing aerosol dry powder. The amount provided by each operation of the valve may be metered according to any method known in the art.

The following examples are given to further set forth more specific aspects of the invention but are not to be interpreted in a limiting sense.

The components may be combined as set forth in the discussion of "Aerosol Formulations with Flunisolide Hemihydrate" The hemihydrate need not be prepared before formulation since conversion to that form takes place upon contact with the propellant.

| | |
|---|---|
| Example I - Aerosol | |
| Flunisolide (particle size range of 1 to 5 microns) | 3.0% |
| Span ® 85 (sorbitan trioleate) | 1.0 |
| Freon ® 11 (trichloromonofluoromethane) | 30.0 |
| Freon ® 114 (dichlorotetrafluoroethane) | 41.0 |
| Freon ® 12 (dichlorodifluoromethane) | 25.0 |
| Example II - Aerosol | |
| Flunisolide, (particle size range of 1-5 microns) | 0.5% |
| Span 85 | 0.5% |
| Propellant B[1] | 99.0% |

[1]Propellant B consists of 10% Freon 11, 50.4% Freon 114, 31.6% Freon 12, and 8.0% butane.

| | |
|---|---|
| Example III - Aerosol | |
| Flunisolide | 1.00% |
| Span 85 | 0.25% |
| Freon 11 | 5.0% |
| Freon W[1] | 93.75% |

[1]Freon W consists of 61.5% Freon 114 and 38.5% Freon 12.

| | |
|---|---|
| Example IV - Aerosol | |
| Flunisolide | 0.50% |
| Span 80 | 0.50% |
| Propellant (C)[1] | 99.0% |

[1]Propellant C consists of 30.0% Freon 11 and 70% Freon W.

| | |
|---|---|
| Example V - Aerosol | |
| Flunisolide | .88% |
| Sodium sulfate (anhydrous), micronized | .88 |
| Span 85 | 1.00 |
| Propellant consisting of 50% Freon 12, 25% Freon 11, and 25% Freon 114 | 97.24% |
| Example VI - Aerosol | |
| Flunisolide | 0.6% |
| Span 85 | 0.5% |
| Freon 11 | 20.0% |
| Freon 12/Freon 114 (20/80) | 78.9% |

Example VII

Preparation of Flunisolide Hemihydrate

122 Grams of flunisolide, a mixture of primarily Form B with some Form A material, was dissolved in 800 ml methylene chloride. The resulting solution was filtered to remove any solid material. To the resulting solution 1200 ml of iso-octane (2,2,4-trimethyl pentane) was added and allowed to stand at room temperature for two hours. The resulting precipitate was evaporated to 1000 ml by heating on a steam bath and allowed to stand overnight at room temperature. The resulting precipitate was filtered, dried, then analyzed via X-ray diffractometer as discussed herein. The precipitate was found to have substantially the same X-ray diffraction pattern as set forth in Table A above. The same pattern was observed after micronization of this material.

Example VIII

Preparation of Flunisolide Hemihydrate

The same procedure as set forth in Example VII was followed except that the solution of flunisolide in methylene chloride was poured into the iso-octane. Upon X-ray analysis, the resulting precipitate was found to have substantially the same X-ray diffraction pattern as set forth in Table A.

Example IX

Preparation of Flunisolide Hemihydrate

Fifty (50) grams (g) of water damp flunisolide are placed in a 1 liter Erlenmeyer flask provided with magnetic stirring, and 250 milliliters (ml) of damp n-butanol is added. The mixture is heated to 70° on a steam bath until complete dissolution is achieved and then the solution is left to cool slowly at approximately 1 degree per minute. At about 35° C. crystallization becomes apparent and at 30° C. n-heptane is slowly added over a period of about 1 hour until the total volume of the mixture is 1 liter. After stirring for a further hour at ambient temperature, the product is filtered, washed several times with n-heptane and air dried. The material is then dried in a vacuum oven at 50° C. for three days to yield 45 grams of flunisolide having a powder X-ray diffraction pattern set forth in Table A.

Analysis of the crystals using Karl Fischer reagent in Photovolt's Aquatest IV gives 1.93% w water.

Example X

One hundred (100) grams of flunisolide are placed in a 500 ml Erlenmeyer flask provided with magnetic stirring, and 196 ml analytical grade n-butanol and 4 ml distilled water are added. The mixture is heated with stirring to 95° C. until complete dissolution is achieved, then cooled with stirring. At about 70° crystallization becomes apparent. The resulting slurry is cooled to room temperature and stirred overnight. The product is then filtered and air-dried, yielding 85 g flunisolide having the powder x-ray diffraction pattern set forth in Table A.

Analysis of the resulting crystals using Karl Fischer reagent in Photovolt's Aquatest IV gives 1.93% w water.

Example XI

Ten (10) grams of flunisolide are placed in a 50 ml Erlenmeyer flask provided with magnetic stirring and 15 ml n-propanol plus 0.6 ml distilled water added. The mixture is heated with stirring to 90° C. until complete dissolution is achieved, then cooled with stirring. Crystallization becomes apparent at about 60°, and the resulting slurry is cooled with stirring to room temperature. After overnight stirring at room temperature, the product is filtered and air dried, giving 8.6 g flunisolide having the powder x-ray diffraction pattern set forth in Table A.

Analysis of the crystals using Karl Fischer reagent in Photovolt's Aquatest IV gives 2.08% w water.

Example XII

Ten (10) grams flunisolide are placed in a 50 ml Erlenmeyer flask equipped with magnetic stirring and 20 ml isopropanol and 1 ml distilled water added. This mixture is heated to about 70° C. until a clear solution is obtained, then cooled with stirring. Crystallization becomes evident at 50°-60° C. The resulting slurry is cooled to room temperature and stirred overnight. After standing for 6 days at room temperature, filtering, air drying, drying in vacuo at room temperature for 24 hours, 8.5 g of flunisolide is obtained having the powder x-ray diffraction pattern set forth in Table A.

Analysis of the crystals using Karl Fischer reagent in Photovolt's Aquatest IV gives 2.18% water.

We claim as our invention:

1. A compound of the formula

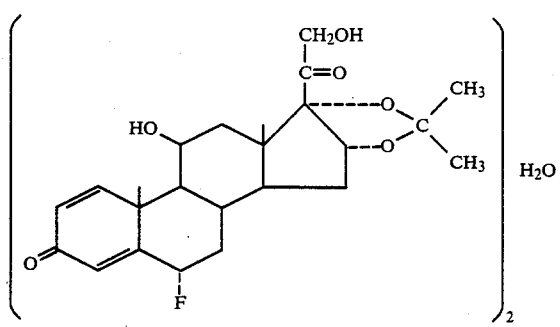

i.e. 6α-fluoro-11β,21-dihydroxy-16α,17α-isopropylidene dioxypregna-1,4-diene-3,20-dione hemihydrate.

2. A method for treating a respiratory disease in a mammal which comprises administering to said mammal by inhalation a therapeutically effective amount of the compound of claim 1 as an aerosol.

3. The method of claim 2 wherein the compound of claim 1 is administered as an aerosol formed from a mixture comprising a therapeutically effective amount of said crystalline form suspended in a pharmaceutically acceptable propellant containing an effective amount of a surfactant.

4. The method of claim 3 wherein said propellant comprises monofluorotrichloromethane, dichlorodifluoromethane, dichlorotetrafluoroethane or mixtures thereof.

5. The method of claim 4 wherein at least one pharmaceutically acceptable, propellant, in addition to those set forth in claim 4, is included in said aerosol.

6. A composition useful for treating a respiratory disease in a mamal comprising (a) 0.01 to about 20% by weight of a compound of the formula

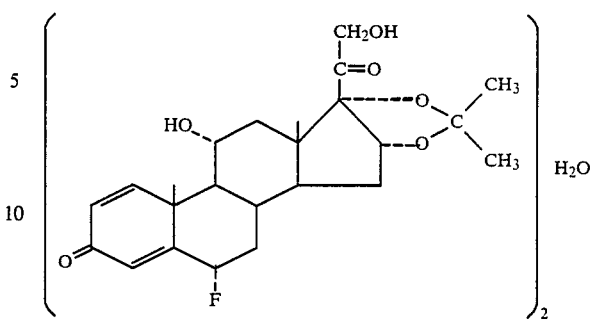

i.e. 6α-fluoro-11β,21-dihydroxy-16α,17α-isopropylidene dioxypregna-1,4-diene-3,20-dione hemihydrate having a particle size less than 100 microns, (b) about 0.1 to about 20% by weight of a suitable surfactant, and (c) the remainder a pharmaceutically acceptable, liquid aerosol propellant.

7. The composition of claim 6 wherein said aerosol propellant is a pharmaceutically acceptable fluorinated or fluorochlorinated lower alkane.

8. The composition of claim 3 wherein said lower alkane is chosen from the group consisting of monofluorotrichloromethane, dichlorodifluoromethane, dichlorotetrafluoroethane, and mixtures thereof.

9. The composition of claim 6 wherein said composition is kept under pressure as an aerosol bomb.

10. The composition of claim 2 which comprises
  (a) about 0.04% w to about 1.0% w of the compound of claim 1 having a particle size less than 25 microns;
  (b) about 97.5% w to about 99.21% w of said propellant; and
  (c) about 0.25% w to 1.5% w of sorbitan trioleate.

11. The composition of claim 10 wherein said propellant consists of 50% by weight dichlorodifluoromethane, 25% by weight trichloromonofluoromethane, and 25% by weight dichlorotetrafluoroethane.

* * * * *

UNITED STATES PATENT AND TRADEMARK OFFICE
CERTIFICATE OF CORRECTION

PATENT NO. : 4,933,168

DATED : June 12, 1990

INVENTOR(S) : Jones et al.

It is certified that error appears in the above-identified patent and that said Letters Patent is hereby corrected as shown below:

Claim 8, at column 14, line 25 "claim 3" should read --claim 7--.

Claim 10, at column 14, line 31 "claim 2" should read --claim 6--.

Signed and Sealed this

Twentieth Day of August, 1996

Attest:

BRUCE LEHMAN

*Attesting Officer*     *Commissioner of Patents and Trademarks*